US011389808B2

(12) United States Patent
Sunshine

(10) Patent No.: US 11,389,808 B2
(45) Date of Patent: Jul. 19, 2022

(54) ION GENERATOR DEVICE SUPPORTS

(71) Applicant: PLASMA AIR INTERNATIONAL, INC, Stamford, CT (US)

(72) Inventor: Lawrence T. Sunshine, Stamford, CT (US)

(73) Assignee: Plasma Air International, Inc., Stamford, CT (US)

( * ) Notice: Subject to any disclaimer, the term of this patent is extended or adjusted under 35 U.S.C. 154(b) by 501 days.

(21) Appl. No.: 16/071,245

(22) PCT Filed: Jan. 19, 2017

(86) PCT No.: PCT/US2017/014103
§ 371 (c)(1),
(2) Date: Jul. 19, 2018

(87) PCT Pub. No.: WO2017/127523
PCT Pub. Date: Jul. 27, 2017

(65) Prior Publication Data
US 2021/0197208 A1    Jul. 1, 2021

Related U.S. Application Data

(60) Provisional application No. 62/286,088, filed on Jan. 22, 2016, provisional application No. 62/280,580, filed on Jan. 19, 2016.

(51) Int. Cl.
| | | |
|---|---|---|
| *B03C 3/86* | (2006.01) |
| *B03C 3/38* | (2006.01) |
| *H01J 7/24* | (2006.01) |
| *H01T 23/00* | (2006.01) |

(52) U.S. Cl.
CPC ............... *B03C 3/86* (2013.01); *B03C 3/38* (2013.01); *H01J 7/24* (2013.01); *H01T 23/00* (2013.01); *H01J 2237/2566* (2013.01)

(58) Field of Classification Search
CPC ........ A61N 1/44; A61N 1/0428; A61N 1/325; A61N 2005/0644; A61N 2005/0652; A61N 2005/0663; A61N 5/0616; A61N 1/10; A61N 1/322; A61N 5/1028; H01T 23/00; A61L 9/22; A61L 2209/15; A61L 2209/16; B03C 3/86; B03C 3/38; H01J 7/24; H01J 2237/2566; B01D 53/323; B01D 2258/06; B01D 2259/80; B01D 53/32
See application file for complete search history.

(56) References Cited

U.S. PATENT DOCUMENTS

| 3,875,461 A | 4/1975 | Richardson et al. |
| 9,660,425 B1 | 5/2017 | Sunshine |
(Continued)

OTHER PUBLICATIONS

Search Report dated Sep. 11, 2019 received in European Patent Application No. 17741909.0.
(Continued)

*Primary Examiner* — Tracie Y Green
(74) *Attorney, Agent, or Firm* — Withrow & Terranova, PLLC

(57) ABSTRACT

The present disclosure is directed to ion generator device supports. An ion generator device support is configured to retain an ion generator device in a cavity formed by a plurality of walls of the ion generator device support.

22 Claims, 8 Drawing Sheets

(56) References Cited

U.S. PATENT DOCUMENTS

| | | | |
|---|---|---|---|
| 2004/0145853 A1* | 7/2004 | Sekoguchi | A61L 9/22 361/225 |
| 2005/0117269 A1* | 6/2005 | Nakasone | H01T 23/00 361/231 |
| 2008/0278881 A1 | 11/2008 | Kato et al. | |
| 2012/0287551 A1 | 11/2012 | Waddell et al. | |
| 2015/0253019 A1 | 9/2015 | Waddell | |

OTHER PUBLICATIONS

International Search Report and Written Opinion dated May 18, 2017 issued in PCT/US2017/014103.
Official Action dated Aug. 16, 2019 received from the Chinese Patent Office in related application CN 2017800184187.

* cited by examiner

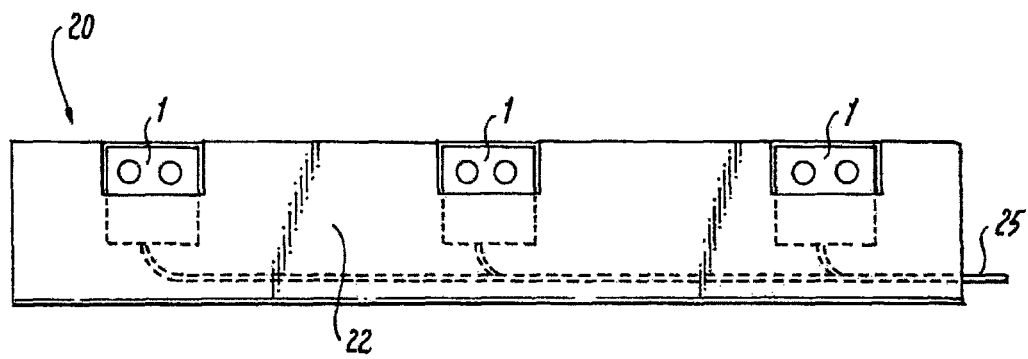
Fig. 2A
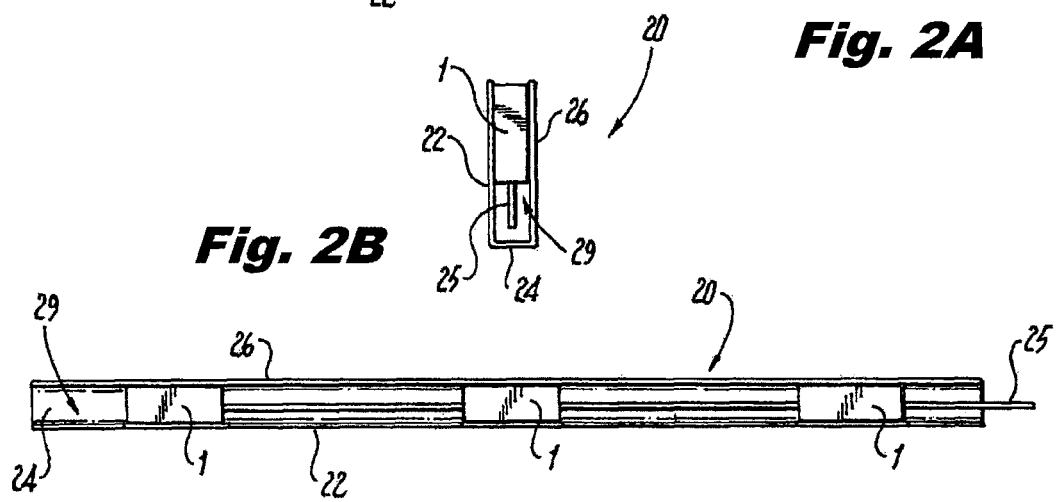
Fig. 2B
Fig. 2C
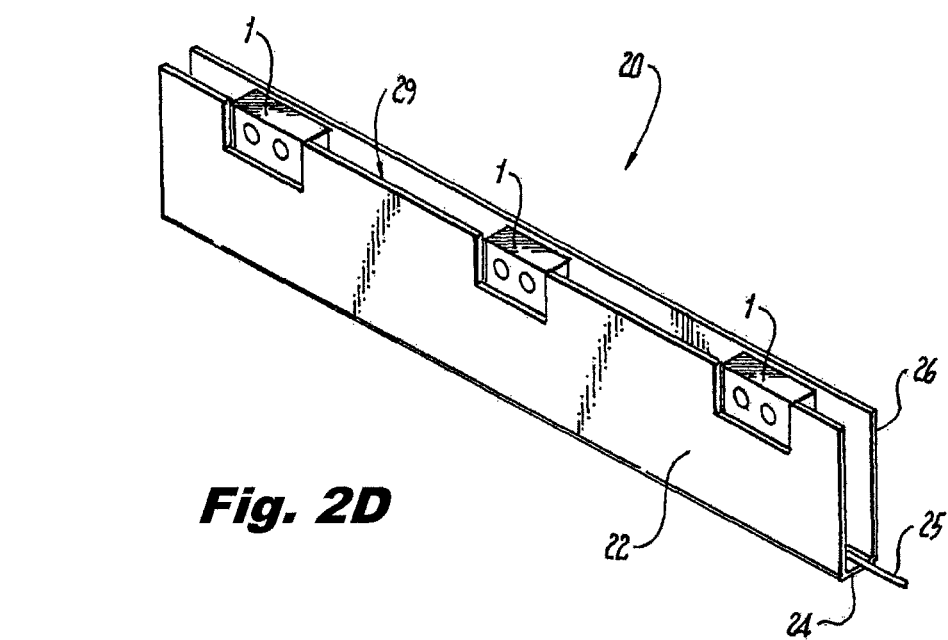
Fig. 2D

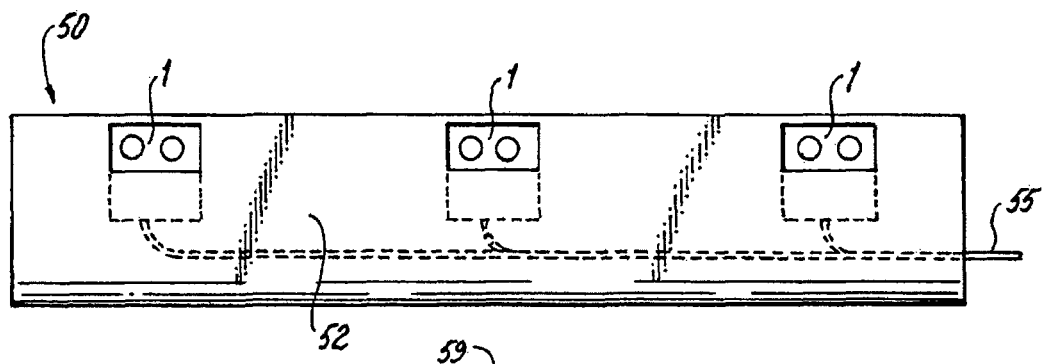
Fig. 5A
Fig. 5B
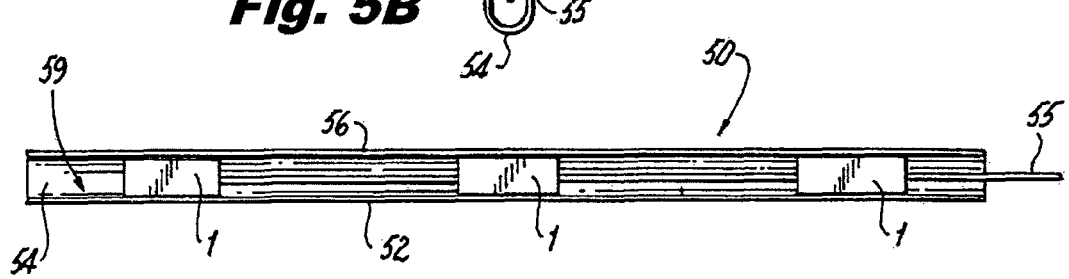
Fig. 5C
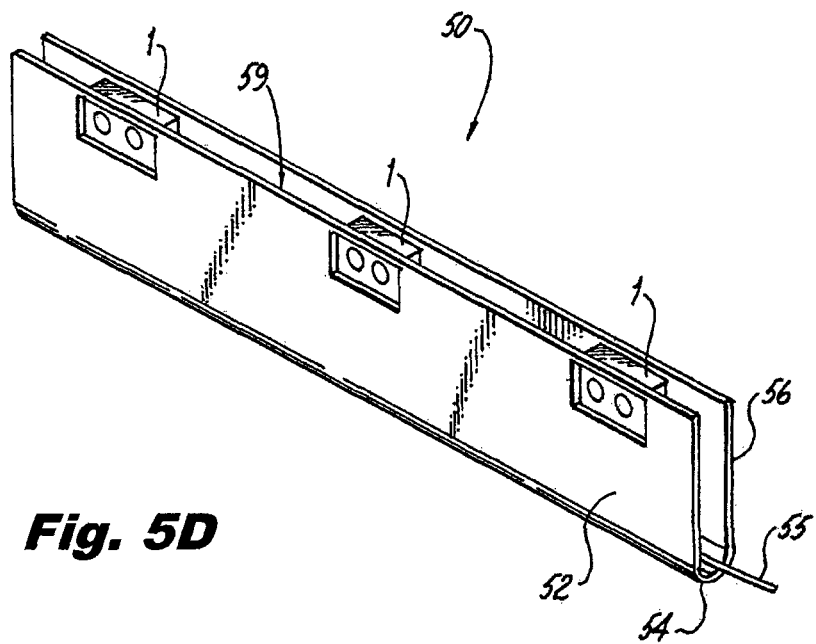
Fig. 5D

ION GENERATOR DEVICE SUPPORTS

FIELD OF THE DISCLOSURE

The present disclosure is directed to ion generator device supports (enclosures, mounts and apparatus) that are configured to hold one or more ion generator devices. The present disclosure is further directed to ion generator device supports that are configured to be placed on, in, or a combination of on and in heating, ventilating and air-conditioning (HVAC) elements, including but not limited to Roof Top Units (RTUs), air handling units (AHU), fan coil units (FCU), Variable Refrigerant Volume Units (VRVU), Variable Refrigerant Flow Units (VRFU) and Packaged Terminal Air Conditioner (PTAC) units, and also including heat pumps, ducts, air inlets, and air outlets.

BACKGROUND OF THE DISCLOSURE

An air ionizer typically includes electrodes to which high voltages are applied. Gas molecules near the electrodes become ionized when they either gain or lose electrons. Because the ions take on the charge of the nearest electrode, and like charges repel, they are repelled from that electrode. In typical air ionizers, an air current is introduced to the device in order to carry the ions away from the electrodes to a "target region" where an increased ion content is desired.

Ions in the air are attracted to objects carrying an opposite charge. When an ion comes in contact with an oppositely charged object, it exchanges one or more electrons with the object, lessening or eliminating the charge on the object. Thus, ions in the air can reduce contamination of objects in the environment.

SUMMARY OF THE DISCLOSURE

The present disclosure is directed to ion generator device supports. An ion generator device support is configured to retain an ion generator device in a cavity formed by a plurality of walls of the ion generator device support.

BRIEF DESCRIPTION OF THE DRAWINGS

The present disclosure will be better understood by reference to the following drawings of which:

FIG. 1A is a plan view. FIG. 1B is an edge view; FIG. 1C is a side view; FIG. 1D is a perspective view;

FIGS. 2A-2D depict an ion generator device support holding representative ion generator devices according to another aspect of the disclosure. FIG. 2A is a plan view. FIG. 2B is an edge view; FIG. 2C is a side view; FIG. 2D is a perspective view;

FIG. 3A is a plan view. FIG. 3B is an edge view; FIG. 3C is a side view; FIG. 3D is a perspective view;

FIG. 4A is a plan view. FIG. 4B is an edge view; FIG. 4C is a side view; FIG. 4D is a perspective view;

FIGS. 5A-5D depict an ion generator device support holding representative ion generator devices according to another aspect of the disclosure. FIG. 5A is a plan view. FIG. 5B is an edge view; FIG. 5C is a side view; FIG. 5D is a perspective view;

FIG. 6A is a plan view. FIG. 6B is an edge view; FIG. 6C is a side view; FIG. 6D is a perspective view;

FIG. 7A is a plan view. FIG. 7B is an edge view; FIG. 7C is a side or bottomview; FIG. 7D is a perspective view; FIG. 8A is a plan view. FIG. 8B is an edge view; FIG. 8C is a side or bottom view; FIG. 8D is a perspective view.

DETAILED DESCRIPTION OF THE DISCLOSURE

The disclosure includes an ion generator device support that can be used to support ion generator devices for any suitable purpose, including placement on, in, or a combination of on and in heating, ventilating and air-conditioning (HVAC) elements, including but not limited to Roof Top Units (RTUs), air handling units (AHU), fan coil units (FCU), Variable Refrigerant Volume Units (VRVU), Variable Refrigerant Flow Units (VRFU) and Packaged Terminal Air Conditioner (PTAC) units, and also including heat pumps, ducts, air inlets, and air outlets.

Other suitable purposes for use of the disclosed ion generator device support is placement on, in, or a combination of on and in hand dryers, hair dryers, vacuum cleaners, variable air volume diffusers, refrigerators, freezers, automobile ventilation elements (including cars, trucks, recreational vehicles, campers, boats and planes) and light fixtures.

As used herein, the term "resilient" refers to the capacity of a material to spring back, rebound or return substantially to its original, or nearly original, shape or position after being compressed, deformed, distorted, bent or stretched.

As used herein, the term "about" indicates that the value listed may be somewhat altered, as long as the alteration does not result in nonconformance of the process or structure to the illustrated embodiment. For example, for some elements the term "about" can refer to a variation of ±0.1%, for other elements, the term "about" can refer to a variation of ±1% or ±10%, or any point therein.

As used herein, the term "substantially" refers to the complete or nearly complete extent or degree of an action, characteristic, property, state, structure, item, or result. For example, an object that is "substantially" parallel would mean that the object is either completely parallel or nearly completely parallel. The exact allowable degree of deviation from absolute completeness may in some cases depend on the specific context. However, generally speaking the nearness of completion will be so as to have the same overall result as if absolute and total completion were obtained.

Throughout this application, the portions of the ion generator device supports can be made from any suitable material, including suitable plastics, such as polycarbonates, vinyls, polyethylenes, polyvinyl chloride, polypropylene, acrylonitrile butadiene styrene (ABS) and polystyrene, suitable metals including galvanized steel, stainless steel and aluminum, natural and synthetic rubbers, and combinations thereof.

Figure 1A:
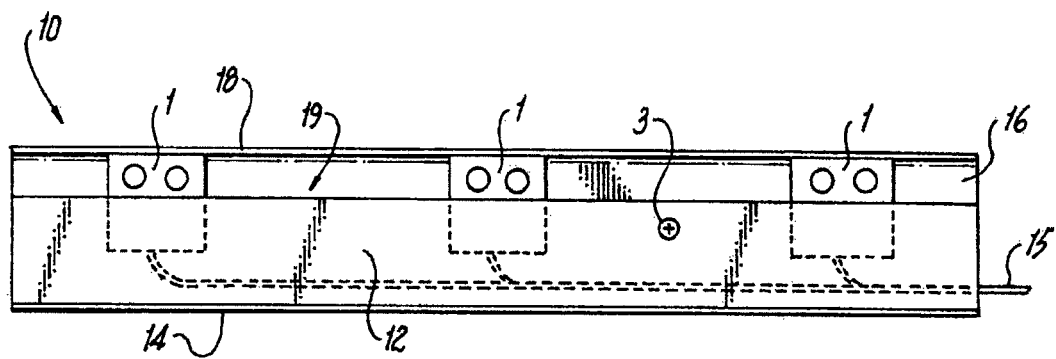
FIGS. 1A-1D depict an ion generator device support holding representative ion generator devices according to an aspect of the disclosure.
Figure 1B:
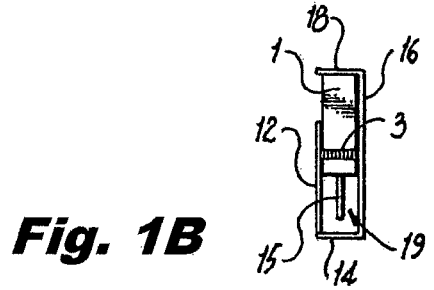

FIG. 1A of the present disclosure is a plan view of a portion of one embodiment of the present disclosure. FIG. 1B of the present disclosure of an edge view of ion generator device support 10, which includes a first wall 12, a second wall 14, a third wall 16 that extends orthogonally from the second wall 14 and is opposed to the first wall 12, and a fourth wall 18 that extends orthogonally from the third wall 16 opposed to the second wall 14. Ion generator device support 10 includes an open cavity 19 formed between the second wall 14, the third wall 16 and the fourth wall 18. Open cavity 19 is configured to accommodate therein an ion generator installed in an operable position.

The ion generator device is a device capable of producing positive ions, negative ions or a combination of positive ions and negative ions, such as from an ionizing needle, from an ionizing brush and from an ionizing tube, at various intensities as desired. The ion generator device can include ionizing needle elements, which are rod shaped and come to a point at one end. Alternatively, the ion generator device can include ionizing brushes, which can contain a plurality of bristles or fibers formed of a conductive material. Alternatively, the ion generator device can include ionizing tubes, which includes a tube that is surrounded by at least one electrode that is capable of producing positive ions, negative ions or a combination of positive ions and negative ions. Each of the ionizing needle, ionizing brush and ionizing tube can include components formed of a material sufficient to emit ions, such as, for example, a conductive metal, a conductive polymer, a conductive semi-fluid and a carbon material. One such embodiment of this ion generator is shown and described in U.S. patent application Ser. No. 14/983,846, which is incorporated herein by reference.

In the figures each ion generator device includes a first portion, which is visible in the figures, and a second portion, which is indicated with dashed lines in FIGS. 1A, 2A, 3A, 4A, 5A, 6A, 7A and 8A. In the figures each ion generator device also includes electrodes in the first portion, indicated as circular in the figures for illustrative purposes.

FIG. 1A shows, for example, three ion generators 1 installed in open cavity 19. Although the first wall 12 is shown as facing frontwards in FIG. 1A, this is for illustrative purposes only and each figure of an ion generator device support throughout the application can be rotated into any suitable orientation. In some embodiments, the ion generator device support 10 will be installed with open cavity 19 facing downwards.

In this embodiment, the third wall 16 can include a first portion and a second portion, such that when the ion generator device 1 is retained within the open cavity 19, the ion generator device 1 being adjacent the first portion of the third wall 16 and one or more wires 15 connecting the ion generator device 1 to a power supply (not shown), external to the ion generator device support 10 and being adjacent to the second portion of the third wall 16.

As can be seen from FIG. 1B, the first wall 12 extends a smaller distance from the second wall 14 as compared to the third wall 16. Although first wall 12 is illustrated as extending a majority of the distance between second wall 14 and third wall 16, first wall 12 can be any suitable distance that is smaller than the distance from the second wall 14 to the third wall 16 to configure open cavity 19 to accept an ion generator therein.

In FIG. 1A, the open cavity 19 can include two areas, a substantially open cavity, which includes the visible portion of ion generator device 1, and a substantially closed cavity, which includes the portion of ion generator device 1 shown in dashed lines. In FIG. 1B, the substantially open cavity is defined by fourth wall 18, third wall 16 and an edge of the first wall 12 that is furthest from the second wall 14. The substantially closed cavity is defined by the first wall 12, the second wall 14 and the third wall 16.

In FIG. 1A, a securing element 3 maintains first wall 12 in contact with ion generator 1. Securing element 3 can be any suitable element capable of maintaining first wall 12 in relation to third wall 16, such as a screw, rivet, nail, an adhesive, or the like. In this embodiment one securing element 3 is shown, but in other embodiments, two or more securing elements 3 can extend from first wall 12 to third wall 16.

As shown in FIG. 1B and subsequent figures, the first wall 12 is substantially parallel to the third wall 16 and the second wall 14 is substantially parallel to the fourth wall 18, but, in other embodiments, first wall 12 and third wall 16 and second wall 14 and fourth wall 18 can be formed at relative angles to each other. Also as shown in FIG. 1B and subsequent figures, the second wall 14 and the third wall 16, and the third wall 16 and the fourth wall 18 are substantially perpendicular to each other, but, in other embodiments, second wall 14 and the third wall 16 and the third wall 16 and the fourth wall 18 can be formed at relative angles to each other.

First wall 12, second wall 14, third wall 16 and fourth wall 18 can be formed of the same material, or of different materials from each other. The same or different materials can be any suitable material, including suitable plastics, such as polycarbonates, vinyls, polyethylenes, polyvinyl chloride, polypropylene, acrylonitrile butadiene styrene (ABS) and polystyrene, suitable metals including galvanized steel, stainless steel and aluminum, natural and synthetic rubbers, and combinations thereof.

One or more of first wall 12, second wall 14, third wall 16 and fourth wall 18 can be formed of a resilient material, such that when they are compressed, deformed, distorted, bent or stretched, they have the capacity to spring back, rebound or return substantially to its original, or nearly original, shape or position.

In this embodiment three ion generator devices 1 are shown, but in other embodiments, ion generator device support 10 can include, one ion generator, two ion generator, or up to several tens of ion generator devices.

In FIG. 1B, the securing element 3 can be seen extending from first wall 12 to third wall 16.

Figure 1C:
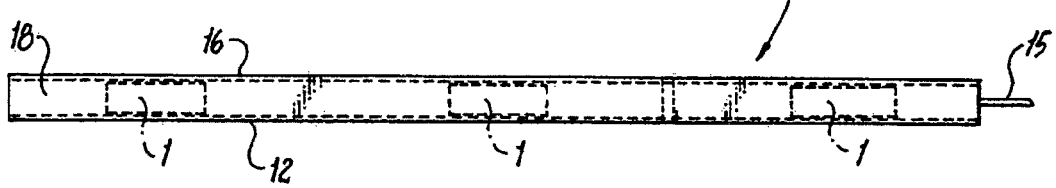

In FIG. 1C, a side view of a portion of ion generator device support 10 is shown, specifically, the side of fourth wall 18. In FIG. 1C the edge vertically higher is the edge where fourth wall 18 meets third wall 16.

Figure 1D:
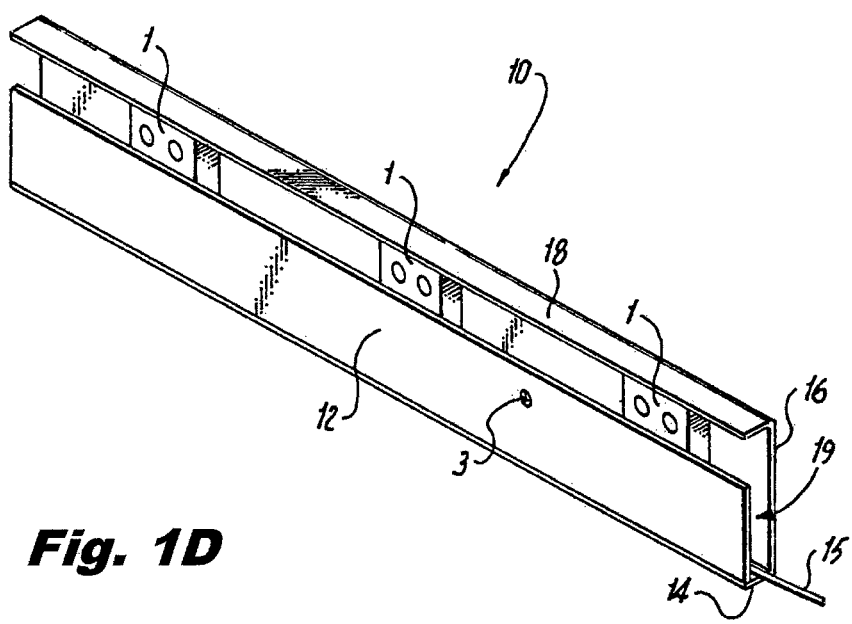

In FIG. 1D, a perspective view of ion generator device support 10 is shown.

FIG. 2A of the present disclosure is a plan view of a portion of one embodiment of the present disclosure. FIG. 2B illustrates ion generator device support 20, which includes a first wall 22, a second wall 24 that extends orthogonally from the first wall 22 and a third wall 26 that extends orthogonally from the second wall 24 opposed to the first wall 22.

Ion generator device support 20 includes an open cavity 29 formed between the first wall 22, the second wall 24 and the third wall 26. Open cavity 29 is configured to accommodate therein an ion generator installed in an operable position.

FIG. 2A shows, for example, three ion generators 1 installed in open cavity 29. Although the first wall 22 is shown as facing frontwards in FIG. 1A, this is for illustrative purposes only and each figure of an ion generator device support throughout the application can be rotated into any suitable orientation.

As can be seen from FIG. 2A, a portion of first wall 22 is removed, or is not included as part of first wall 22, so that a portion of ion generator 1 can be exposed. This portion of the first wall 22 that has been removed can be of a smaller or larger size in other embodiments, to accommodate other ion generators, along the edge of first wall 22.

In FIG. 2A, the open cavity 29 can include two areas, a substantially open cavity, which includes the visible portion of ion generator device 1, and a substantially closed cavity, which includes the portion of ion generator device 1 shown in dashed lines. In FIG. 2B, the substantially open cavity is defined by the opening in the first wall 22, the second wall 24 and the third wall 26. The substantially closed cavity is defined by the first wall 22, the second wall 24 and the third wall 26.

In this embodiment, the third wall 26 can include a first portion and a second portion, such that when the ion generator device 1 is retained within the open cavity 29, the ion generator device 1 being adjacent the first portion of the third wall 26 and one or more wires 25 connecting the ion generator device 1 to a power supply (not shown), external to the ion generator device support 20 and being adjacent to the second portion of the third wall 26.

As shown in FIG. 2B and subsequent figures, the first wall 22 is substantially parallel to the third wall 26, but, in other embodiments, first wall 22 and third wall 26 can be formed at relative angles to each other. Also as shown in FIG. 2B and subsequent figures, the first wall 22 and the second wall 24, and the second wall 24 and the third wall 26 are substantially perpendicular to each other, but, in other embodiments, first wall 22 and the second wall 24, and the second wall 24 and the third wall 26 can be formed at relative angles to each other.

First wall 22, second wall 24 and third wall 26 can be formed of the same material, or of different materials from each other. The same or different materials can be any suitable material, including suitable plastics, such as polycarbonates, vinyls, polyethylenes, polyvinyl chloride, polypropylene, acrylonitrile butadiene styrene (ABS) and polystyrene, suitable metals including galvanized steel, stainless steel and aluminum, natural and synthetic rubbers, and combinations thereof.

One or more of first wall 22, second wall 24 and third wall 26 can be formed of a resilient material, such that when they are compressed, deformed, distorted, bent or stretched, they have the capacity to spring back, rebound or return substantially to its original, or nearly original, shape or position.

In this embodiment three ion generator devices 1 are shown, but in other embodiments, ion generator device support 20 can include, one ion generator, two ion generators, or up to several tens of ion generator devices.

In FIG. 2B, a side view of ion generator device support 20 is shown.

In FIG. 2C, a side view of a portion of ion generator device support 20 is shown, specifically, the open cavity 29, such that the second wall 24 is visible. In FIG. 2C the edge vertically higher is third wall 26.

In FIG. 2D, a perspective view of ion generator device support 20 is shown.

Figure 3A:
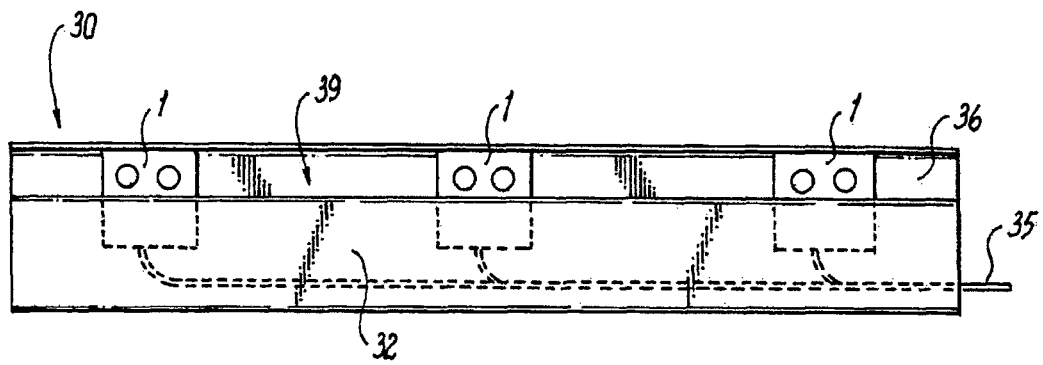
FIGS. 3A-3D depict an ion generator device support holding representative ion generator devices according to another aspect of the disclosure.
Figure 3B:
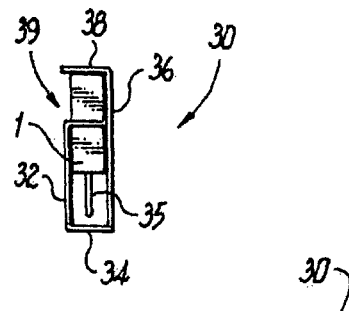

FIG. 3A of the present disclosure is a plan view of a portion of one embodiment of the present disclosure. In FIG. 3B, ion generator device support 30 is shown, which includes a first wall 32, a second wall 34 that extends orthogonally from the first wall 32, a third wall 36 that extends orthogonally from the second wall 34 and is opposed to the first wall 32, and a fourth wall 38 that extends orthogonally from the third wall 36 opposed to the second wall 34.

Extending orthogonally from the first wall 32 is a cover wall 31, which extends at least a majority of the space between the first wall 32 and the third wall 36. Cover wall 31 includes a plurality of segments. Each segment of the cover wall 31 is present along the first wall 32 where ion generators 1 are not to be included in ion generator device support 30. The lengths of segments of cover wall 31 are set to create a predetermined gap between the same, the gap configured and dimensioned to accommodate the width an ion generator device 1. Accordingly, the predetermined gap can be varied as needed to accommodate ion generator devices having different widths.

Ion generator device support 30 includes an open cavity 39 formed between the first wall 32 (between portions of cover wall 31), the second wall 34, the third wall 36 and the fourth wall 38. Open cavity 39 is configured to accommodate therein an ion generator installed in an operable position.

FIG. 3A shows, for example, three ion generators 1 installed in open cavity 39. Although the first wall 32 is shown as facing frontwards in FIG. 3A, this is for illustrative purposes only and each figure of an ion generator device support throughout the application can be rotated into any suitable orientation. In some embodiments, the ion generator device support 30 will be installed with open cavity 39 facing downwards.

In this embodiment, the third wall 36 can include a first portion and a second portion, such that when the ion generator device 1 is retained within the open cavity 39, the ion generator device 1 being adjacent the first portion of the third wall 36 and one or more wires 35 connecting the ion generator device 1 to a power supply (not shown), external to the ion generator device support 30 and being adjacent to the second portion of the third wall 36.

As can be seen from FIG. 3B, the first wall 32 extends a smaller distance from the second wall 34 as compared to the third wall 36. Although first wall 32 is illustrated as extending a majority of the distance between the second wall 34 and third wall 36, first wall 32 can be any suitable distance that is smaller than the distance from the second wall 34 to the third wall 36 to configure open cavity 39 to accept an ion generator therein.

In FIG. 3A, the open cavity 39 can include two areas, a substantially open cavity, which includes the visible portion of ion generator device 1, and a substantially closed cavity, which includes the portion of ion generator device 1 shown in dashed lines. In FIG. 3B, the substantially open cavity is defined by fourth wall 38, third wall 36 and an edge of the first wall 32 (between portions of cover wall 31) that is furthest from the second wall 34. The substantially closed cavity is defined by the first wall 32, the second wall 34 and the third wall 36.

As shown in FIG. 3B and subsequent figures, the first wall 32 is substantially parallel to the third wall 36, the cover wall 31 is substantially parallel to both the second wall 34 and the fourth wall 38, and the second wall 34 is substantially parallel to the fourth wall 38, but, in other embodiments, first wall 32 and third wall 36, cover wall 31 and both the second wall 34 and the fourth wall 38, and second wall 34 and fourth wall 38, each can be formed at relative angles to each other.

Also as shown in FIG. 3B and subsequent figures, the cover wall 31 and the first wall 32, the first wall 32 and the second wall 34, the second wall 34 and the third wall 36, and the third wall 36 and the fourth wall 38, are each substantially perpendicular to each other, but, in other embodiments, cover wall 31 and first wall 32, first wall 32 and second wall 34, second wall 34 and the third wall 36, and the third wall 36 and the fourth wall 38, can each be formed at relative angles to each other.

Cover wall 31, first wall 32, second wall 34, third wall 36 and fourth wall 38 can be formed of the same material, or of different materials from each other. The same or different materials can be any suitable material, including suitable plastics, such as polycarbonates, vinyls, polyethylenes, polyvinyl chloride, polypropylene, acrylonitrile butadiene styrene (ABS) and polystyrene, suitable metals including galvanized steel, stainless steel and aluminum, natural and synthetic rubbers, and combinations thereof.

One or more of cover wall 31, first wall 32, second wall 34, third wall 36 and fourth wall 38 can be formed of a resilient material, such that when they are compressed, deformed, distorted, bent or stretched, they have the capacity to spring back, rebound or return substantially to its original, or nearly original, shape or position.

In this embodiment three ion generator devices 1 are shown, but in other embodiments, ion generator device support 30 can include, one ion generator, two ion generator, or up to several tens of ion generator devices.

In FIG. 3B, a side view of ion generator device support 30 is shown.

Figure 3C:
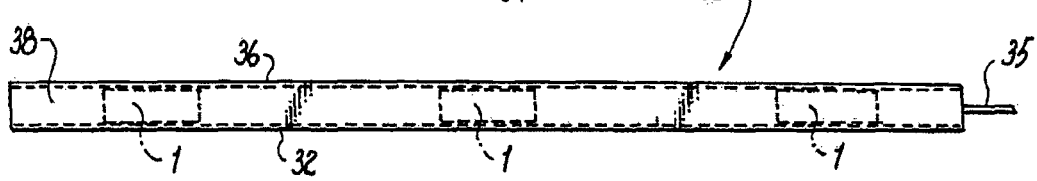

In FIG. 3C, a side view of a portion of ion generator device support 30 is shown, specifically, the side of fourth wall 38. In FIG. 3C the edge vertically higher is the edge where fourth wall 38 meets third wall 36.

Figure 3D:
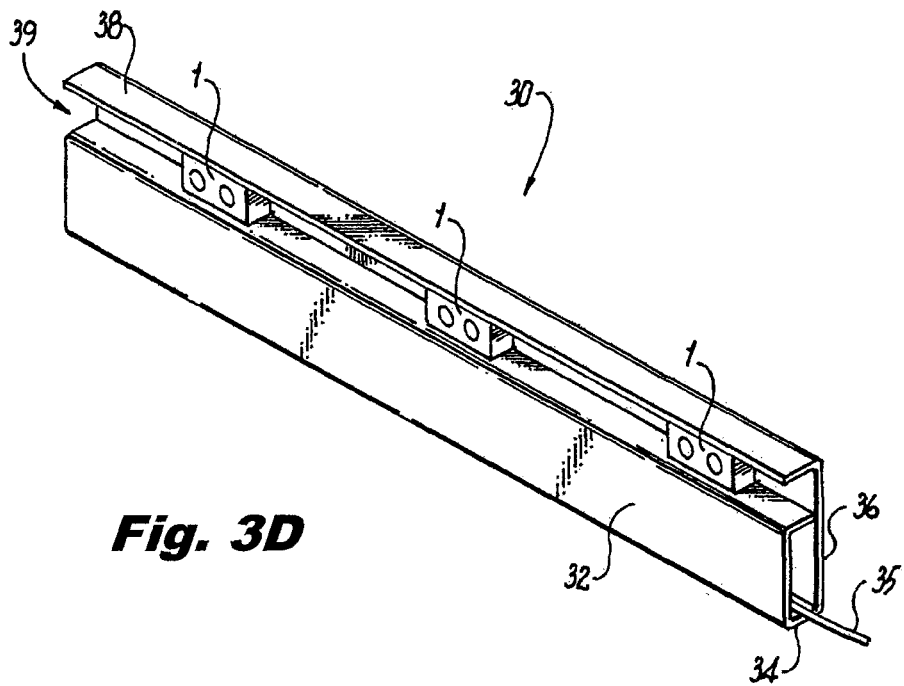

In FIG. 3D, a perspective view of ion generator device support 30 is shown.

Figure 4A:
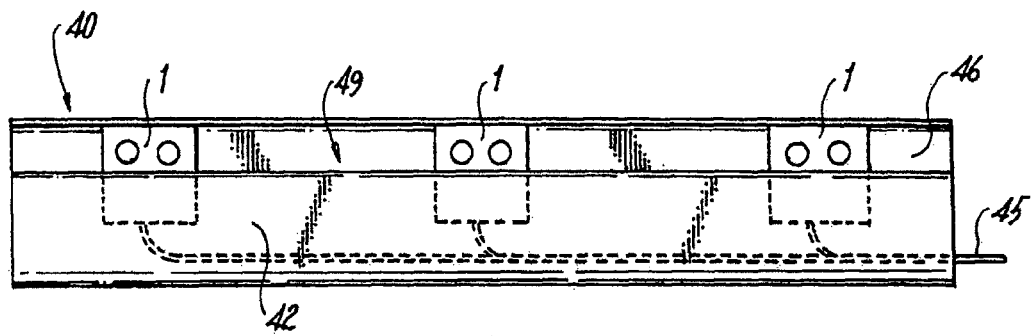
FIGS. 4A-4D depict an ion generator device support holding representative ion generator devices according to another aspect of the disclosure.
Figure 4B:
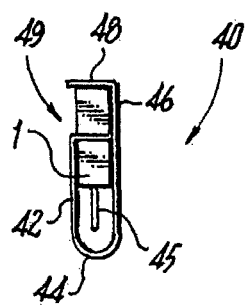

FIG. 4A of the present disclosure is a plan view of a portion of one embodiment of the present disclosure. In FIG. 4B, ion generator device support 40 is shown, which includes a first wall 42, a second wall 44 that extends in a curved shape from the first wall 42 to a third wall 46, the third wall 46 that is opposed to the first wall 42, and a fourth wall 48 that extends orthogonally from the third wall 46.

Extending orthogonally from the first wall 42 is a cover wall 41, which extends at least a majority of the space between the first wall 42 and the third wall 46. Cover wall 41 does not extend along the length of first wall 42, cover wall 41 is configured to be present along the first wall 42 where ion generators 1 are not to be included in ion generator device support 40. The lengths of cover wall 41 along first wall 42 can be configured to accommodate the width of any suitable ion generator device 1.

Ion generator device support 40 includes an open cavity 49 formed between the first wall 42 (between portions of cover wall 41), the second wall 44, the third wall 46 and the fourth wall 48. Open cavity 49 is configured to accommodate therein an ion generator installed in an operable position.

FIG. 4A shows, for example, three ion generators 1 installed in open cavity 49. Although the first wall 42 is shown as facing frontwards in FIG. 4A, this is for illustrative purposes only and each figure of an ion generator device support throughout the application can be rotated into any suitable orientation. In some embodiments, the ion generator device support 40 will be installed with open cavity 49 facing downwards.

In this embodiment, the third wall 46 can include a first portion and a second portion, such that when the ion generator device 1 is retained within the open cavity 49, the ion generator device 1 being adjacent the first portion of the third wall 46 and one or more wires 45 connecting the ion generator device 1 to a power supply (not shown), external to the ion generator device support 40 and being adjacent to the second portion of the third wall 46.

As can be seen from FIG. 4B, the first wall 42 extends a smaller distance from the second wall 44 as compared to the third wall 46. Although first wall 42 is illustrated as extending a majority of the distance between the second wall 44 and third wall 46, first wall 42 can be any suitable distance that is smaller than the distance from the second wall 44 to the third wall 46 to configure open cavity 49 to accept an ion generator therein.

In FIG. 4A, the open cavity 49 can include two areas, a substantially open cavity, which includes the visible portion of ion generator device 1, and a substantially closed cavity, which includes the portion of ion generator device 1 shown in dashed lines. In FIG. 4B, the substantially open cavity is defined by fourth wall 48, third wall 46 and an edge of the first wall 42 (between portions of cover wall 41) that is furthest from the second wall 44. The substantially closed cavity is defined by the first wall 42, the second wall 44 and the third wall 46.

As shown in FIG. 4B and subsequent figures, the cover wall 41 is substantially parallel to the fourth wall 48 and the first wall 42 is substantially parallel to the third wall 46, but, in other embodiments, cover wall 41 and fourth wall 48 and first wall 42 and third wall 46 can be formed at relative angles to each other.

Also as shown in FIG. 4B and subsequent figures, cover wall 41 and first wall 42 are substantially perpendicular to each other, and the third wall 46 and the fourth wall 48 are substantially perpendicular to each other, but, in other embodiments, the cover wall 41 and the first wall 42 can be formed at relative angles to each other and the third wall 46 and the fourth wall 48 can be formed at relative angles to each other.

Also as shown in FIG. 4B and subsequent figures, the second wall 44 has a relatively small radius of curvature, but, in other embodiments the radius of curvature of second wall 44 can be smaller or larger. Also, second wall 44 can be any other suitable shape other than circular, such as elliptical.

Cover wall 41, first wall 42, second wall 44, third wall 46 and fourth wall 48 can be formed of the same material, or of different materials from each other. The same or different materials can be any suitable material, including suitable plastics, such as polycarbonates, vinyls, polyethylenes, polyvinyl chloride, polypropylene, acrylonitrile butadiene styrene (ABS) and polystyrene, suitable metals including galvanized steel, stainless steel and aluminum, natural and synthetic rubbers, and combinations thereof.

One or more of cover wall 41, first wall 42, second wall 44, third wall 46 and fourth wall 48 can be formed of a resilient material, such that when they are compressed, deformed, distorted, bent or stretched, they have the capacity to spring back, rebound or return substantially to its original, or nearly original, shape or position.

In this embodiment three ion generator devices 1 are shown, but in other embodiments, ion generator device support 40 can include, one ion generator, two ion generator, or up to several tens of ion generator devices.

In FIG. 4B, a side view of ion generator device support 40 is shown.

Figure 4C:
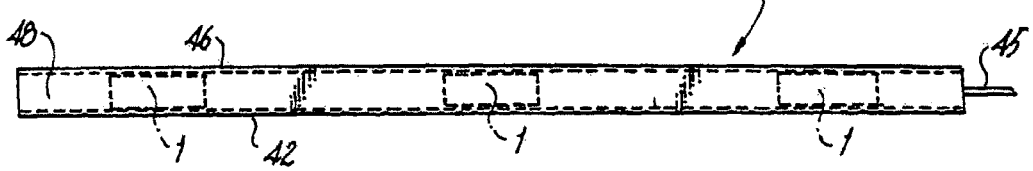

In FIG. 4C, a side view of a portion of ion generator device support 40 is shown, specifically, the side of fourth wall 48. In FIG. 4C the edge vertically higher is the edge where fourth wall 48 meets third wall 46.

Figure 4D:
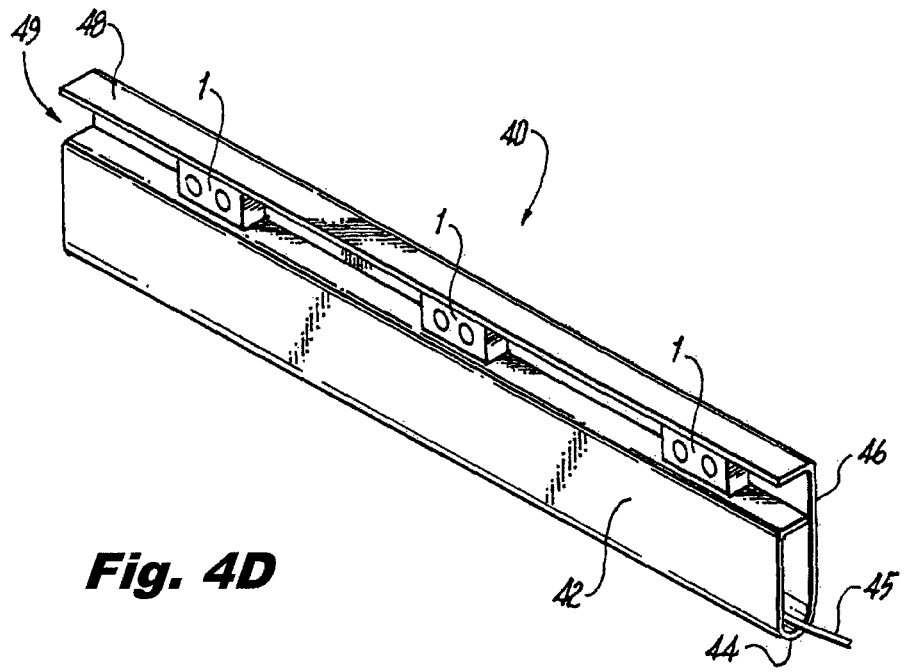

In FIG. 4D, a perspective view of ion generator device support 40 is shown.

FIG. 5A of the present disclosure is a plan view of a portion of one embodiment of the present disclosure. In FIG. 5B ion generator device support 50 is shown, which includes a first wall 52, a second wall 54 that extends in a curved shape from the first wall 52 to a third wall 56, the third wall 56 is opposed to the first wall 52. Ion generator device support 50 includes an open cavity 59 formed between the first wall 52, the second wall 54 and the third wall 56. Open cavity 59 is configured to accommodate therein an ion generator installed in an operable position.

A portion of the ion generator 1 is exposed through a portion of first wall 52, which has been removed or was not originally included in first wall 52. First wall 52 includes an edge 53, which remains as part of the first wall 52 with the portion of the first wall 52 not being present. This portion of the first wall 52 that has been removed can be of a smaller or larger size in other embodiments, to accommodate other ion generators, along the vertically edge of first wall 52.

FIG. 5A shows, for example, three ion generators 1 installed in open cavity 59. Although the first wall 52 is shown as facing frontwards in FIG. 5A, this is for illustrative purposes only and each figure of an ion generator device support throughout the application can be rotated into any suitable orientation. In some embodiments, the ion generator device support 50 will be installed with open cavity 59 facing downwards.

In FIG. 5A, the open cavity 59 can include two areas, a substantially open cavity, which includes the visible portion of ion generator device 1, and a substantially closed cavity, which includes the portion of ion generator device 1 shown in dashed lines. In FIG. 5B, the substantially open cavity is defined by the opening in the first wall 52, the second wall 54 and the third wall 56. The substantially closed cavity is defined by the first wall 52, the second wall 54 and the third wall 56.

In this embodiment, the third wall 56 can include a first portion and a second portion, such that when the ion generator device 1 is retained within the open cavity 59, the ion generator device 1 being adjacent the first portion of the third wall 56 and one or more wires 55 connecting the ion generator device 1 to a power supply (not shown), external to the ion generator device support 50 and being adjacent to the second portion of the third wall 56.

As shown in FIG. 5B and subsequent figures, the first wall 52 is substantially parallel to the third wall 56, but, in other embodiments, first wall 52 and third wall 56 can be formed at relative angles to each other.

Also as shown in FIG. 5B and subsequent figures, the second wall 54 has a relatively small radius of curvature, but, in other embodiments the radius of curvature of second wall 54 can be smaller or larger. Also, second wall 54 can be any other suitable shape other than circular, such as elliptical.

First wall 52, second wall 54 and third wall 56 can be formed of the same material, or of different materials from each other. The same or different materials can be any suitable material, including suitable plastics, such as polycarbonates, vinyls, polyethylenes, polyvinyl chloride, polypropylene, acrylonitrile butadiene styrene (ABS) and polystyrene, suitable metals including galvanized steel, stainless steel and aluminum, natural and synthetic rubbers, and combinations thereof.

One or more of first wall 52, second wall 54 and third wall 56 can be formed of a resilient material, such that when they are compressed, deformed, distorted, bent or stretched, they have the capacity to spring back, rebound or return substantially to its original, or nearly original, shape or position.

In this embodiment three ion generator devices 1 are shown, but in other embodiments, ion generator device support 50 can include, one ion generator, two ion generator, or up to several tens of ion generator devices.

In FIG. 5B, a side view of ion generator device support 50 is shown.

In FIG. 5C, a side view of a portion of ion generator device support 50 is shown, specifically, the open cavity 59, such that the second wall 54 is visible. In FIG. 5C the edge vertically higher is third wall 56.

In FIG. 5D, a perspective view of ion generator device support 50 is shown.

Figure 6A:
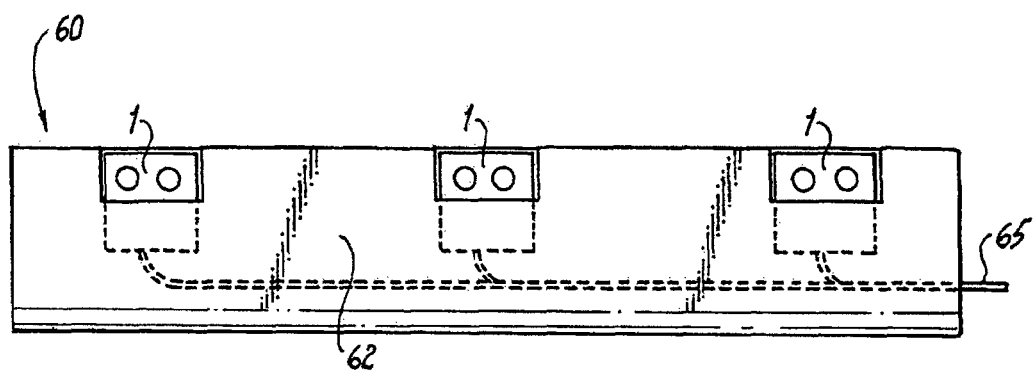
FIGS. 6A-6D depict an ion generator device support holding representative ion generator devices according to another aspect of the disclosure.
Figure 6B:
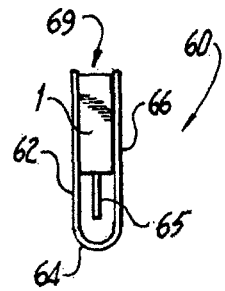

FIG. 6A of the present disclosure is a plan view of a portion of one embodiment of the present disclosure. In FIG. 6B, ion generator device support 60 is shown, which includes a first wall 62, a second wall 64 that extends in a curved shape from the first wall 62 to a third wall 66, the third wall 66 is opposed to the first wall 62. Ion generator device support 60 includes an open cavity 69 formed between the first wall 62, the second wall 64 and the third wall 66. Open cavity 69 is configured to accommodate therein an ion generator installed in an operable position.

A portion of the ion generator 1 is exposed through a portion of first wall 62, which has been removed or was not originally included in first wall 62. This portion of the first wall 62 that has been removed can be of a smaller or larger size in other embodiments, to accommodate other ion generators, along the edge of first wall 62.

FIG. 6A shows, for example, three ion generators 1 installed in open cavity 59. Although the first wall 62 is shown as facing frontwards in FIG. 6A, this is for illustrative purposes only and each figure of an ion generator device support throughout the application can be rotated into any suitable orientation. In some embodiments, the ion generator device support 60 will be installed with open cavity 69 facing downwards.

In FIG. 6A, the open cavity 69 can include two areas, a substantially open cavity, which includes the visible portion of ion generator device 1, and a substantially closed cavity, which includes the portion of ion generator device 1 shown in dashed lines. In FIG. 6B, the substantially open cavity is defined by the opening in the first wall 62, the second wall 64 and the third wall 66. The substantially closed cavity is defined by the first wall 62, the second wall 64 and the third wall 66.

In this embodiment, the third wall 66 can include a first portion and a second portion, such that when the ion generator device 1 is retained within the open cavity 69, the ion generator device 1 being adjacent the first portion of the third wall 66 and one or more wires 65 connecting the ion generator device 1 to a power supply (not shown), external to the ion generator device support 60 and being adjacent to the second portion of the third wall 66.

As shown in FIG. 6B and subsequent figures, the first wall 62 is substantially parallel to the third wall 66, but, in other embodiments, first wall 62 and third wall 66 can be formed at relative angles to each other.

Also as shown in FIG. 6B and subsequent figures, the second wall 64 has a relatively small radius of curvature, but, in other embodiments the radius of curvature of second wall 64 can be smaller or larger. Also, second wall 64 can be any other suitable shape other than circular, such as elliptical.

First wall 62, second wall 64 and third wall 66 can be formed of the same material, or of different materials from each other. The same or different materials can be any suitable material, including suitable plastics, such as polycarbonates, vinyls, polyethylenes, polyvinyl chloride, polypropylene, acrylonitrile butadiene styrene (ABS) and polystyrene, suitable metals including galvanized steel, stainless steel and aluminum, natural and synthetic rubbers, and combinations thereof.

One or more of first wall 62, second wall 64 and third wall 66 can be formed of a resilient material, such that when they are compressed, deformed, distorted, bent or stretched, they have the capacity to spring back, rebound or return substantially to its original, or nearly original, shape or position.

In this embodiment three ion generator devices 1 are shown, but in other embodiments, ion generator device support 60 can include, one ion generator, two ion generator, or up to several tens of ion generator devices.

In FIG. 6B, a side view of ion generator device support 60 is shown.

Figure 6C:
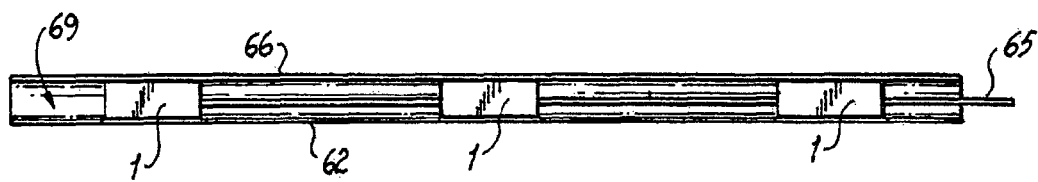

In FIG. 6C, aside view of a portion of ion generator device support 60 is shown, specifically, the open cavity 69, such that the second wall 64 is visible. In FIG. 6C the edge vertically higher is third wall 66.

Figure 6D:
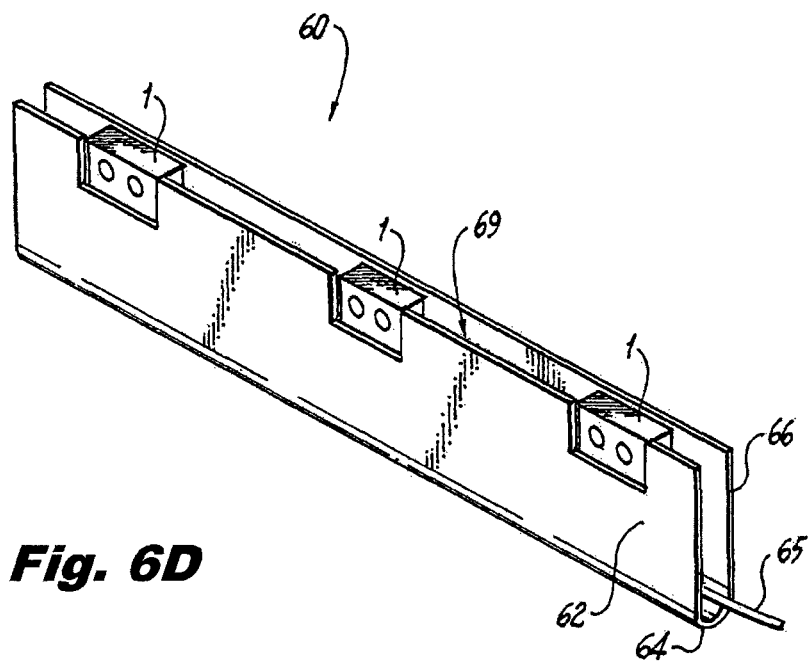

In FIG. 6D, a perspective view of ion generator device support 60 is shown.

Figure 7A:
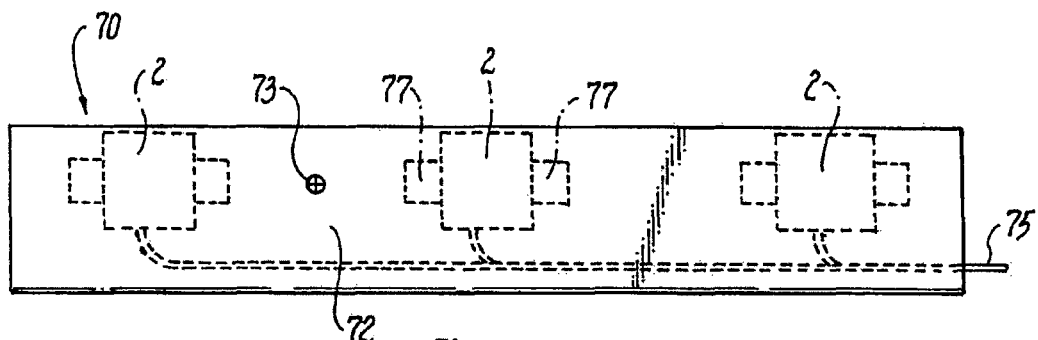
FIGS. 7A-7D depict an ion generator device support holding representative ion generator devices according to another aspect of the disclosure.
Figure 7B:
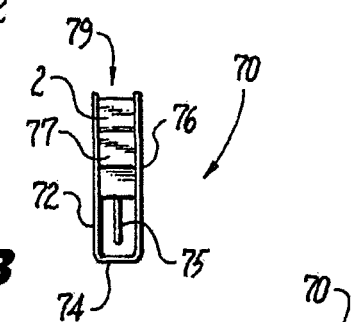

FIG. 7A of the present disclosure is a plan view of a portion of one embodiment of the present disclosure. In FIG. 7B, ion generator device support 70 is shown, which includes a first wall 72, a second wall 74 that extends orthogonally from the first wall 72 and a third wall 76 that extends orthogonally from the second wall 74 opposed to the first wall 72. Ion generator device support 70 includes an open cavity 79 formed between the first wall 72, the second wall 74 and the third wall 76. Open cavity 79 is configured to accommodate therein an ion generator installed in an operable position.

In this embodiment, and each of the other embodiments of this application, the ion generator can be accommodated within the open cavity (in this embodiment open cavity 79) by a friction force applied against the ion generator by one or more walls of the ion generator device support (in this embodiment ion generator device support 70) and/or by an adhesive between the ion generator device and one or more walls of the ion generator device support (in this embodiment ion generator device support 70).

FIG. 7A shows, for example, three ion generators 2 installed in open cavity 79. Although the first wall 72 is shown as facing frontwards in FIG. 7A, this is for illustrative purposes only and each figure of an ion generator device support throughout the application can be rotated into any suitable orientation. In some embodiments, the ion generator device support 70 will be installed with open cavity 79 facing downwards relative to air flow.

Each of the three ion generators 2 can include one or more optional tabs 77, wings or brackets that extend from a side of the ion generators 2 between first wall 72 and third wall 76. A securing mechanism, such as a screw, nail, rivet, Pem® fastener or other substantially rigid element can secure the tab 77, and ion generator 2, to at least one of the first wall 72 and the third wall 76. In other embodiments, the ion generators 2 can be adhered to one or both of the first wall 72 and the third wall 76 and/or be secured by another mechanical element connected to one or both of the first wall 72 and the third wall 76 that is configured to reduce or stop movement of the ion generators along the length of ion generator device support 70.

Also as seen in FIG. 7A, an optional securing element 73 maintains first wall 72 and third wall 76 in contact with ion generator 3. Securing element 73 can be any suitable element capable of maintaining first wall 72 in relation to third wall 76, such as a screw, rivet, nail, an adhesive, Pem® fastener, or the like. In this embodiment one securing element 73 is shown, but in other embodiments, zero, two or more securing elements 73 can extend from first wall 72 to third wall 76. One or both of the first wall 82 and the third wall 86 can include a corresponding opening or hole to receive each securing element 83.

As can be seen from FIG. 7B, a portion of each ion generator 2 is exposed between the first wall 72 and the third wall 76. This portion of each ion generator 2 can be configured to produce ions.

In this embodiment, the third wall 76 can include a first portion and a second portion, such that when the ion generator device 2 is retained within the open cavity 79, the ion generator device 2 being adjacent the first portion of the third wall 76 and one or more wires 75 connecting the ion generator device 2 to a power supply (not shown), external to the ion generator device support 70 and being adjacent to the second portion of the third wall 76.

As shown in FIG. 7B and subsequent figures, the first wall 72 is substantially parallel to the third wall 76, but, in other embodiments, first wall 72 and third wall 76 can be formed at relative angles to each other. Also as shown in FIG. 7B and subsequent figures, the first wall 72 and the second wall 74, and the second wall 74 and the third wall 76 are substantially perpendicular to each other, but, in other embodiments, first wall 72 and the second wall 74, and the second wall 74 and the third wall 76 can be formed at relative angles to each other.

First wall 72, second wall 74 and third wall 76 can be formed of the same material, or of different materials from each other. The same or different materials can be any suitable material, including suitable plastics, such as polycarbonates, vinyls, polyethylenes, polyvinyl chloride, polypropylene, acrylonitrile butadiene styrene (ABS) and polystyrene, suitable metals including galvanized steel, stainless steel and aluminum, natural and synthetic rubbers, and combinations thereof.

One or more of first wall 72, second wall 74 and third wall 76 can be formed of a resilient material, such that when they are compressed, deformed, distorted, bent or stretched, they have the capacity to spring back, rebound or return substantially to its original, or nearly original, shape or position.

In this embodiment three ion generator devices 2 are shown, but in other embodiments, ion generator device support 70 can include, one ion generator, two ion generators, or up to several tens of ion generator devices.

In FIG. 7B, aside view of ion generator device support 70 is shown.

Figure 7C:
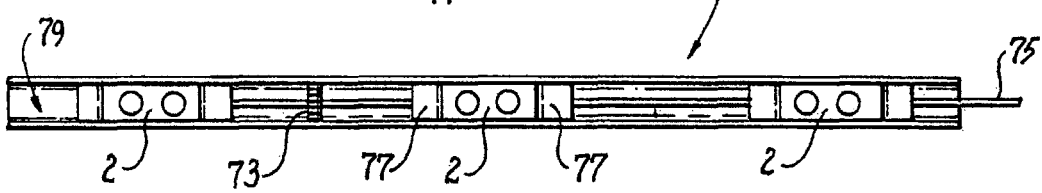

In FIG. 7C, a side or bottom view of a portion of ion generator device support 70 is shown, specifically, the open cavity 79, such that the second wall 74 is visible (where the ion generator devices are not mounted). In FIG. 7C the edge vertically higher is the edge where second wall 64 meets the third wall 76.

Figure 7D:
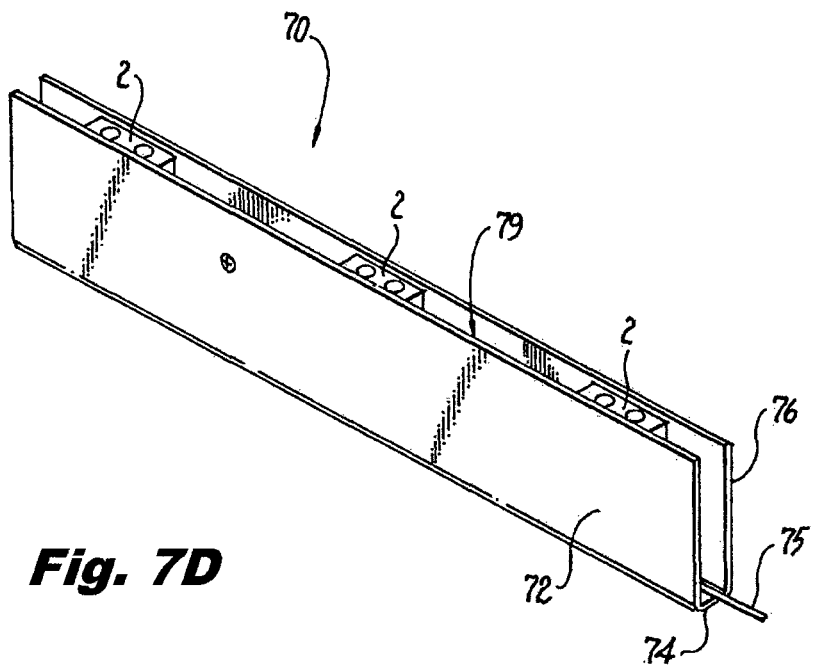

In FIG. 7D, a perspective view of ion generator device support 70 is shown.

Figure 8A:
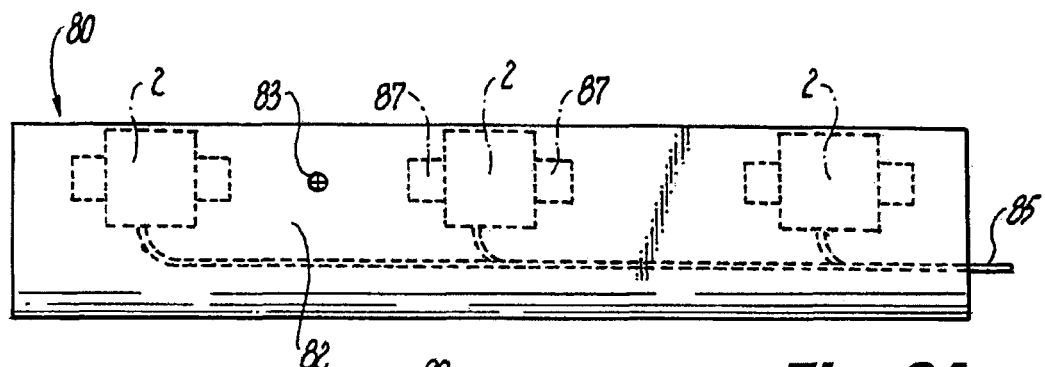
FIGS. 8A-8D depict an ion generator device support holding representative ion generator devices according to another aspect of the disclosure.
Figure 8B:
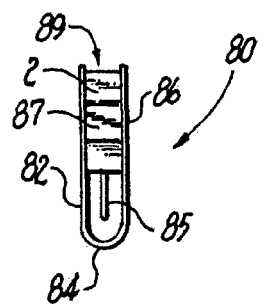

FIG. 8A of the present disclosure is a plan view of a portion of one embodiment of the present disclosure. In FIG. 8B, ion generator device support 80 is shown, which includes a first wall 82, a second wall 84 that extends in a curved shape from the first wall 82 to a third wall 86, the third wall 86 is opposed to the first wall 82. Ion generator device support 80 includes an open cavity 89 formed between the first wall 82, the second wall 84 and the third wall 86. Open cavity 89 is configured to accommodate therein an ion generator installed in an operable position.

As can be seen from FIG. 8A, a portion of each ion generator 2 is exposed between the first wall 82 and the third wall 86. This portion of each ion generator 2 can be configured to produce ions.

FIG. 8A shows, for example, three ion generators 2 installed in open cavity 89. Although the first wall 82 is shown as facing frontwards in FIG. 8A, this is for illustrative purposes only and each figure of an ion generator device support throughout the application can be rotated into any suitable orientation. In some embodiments, the ion generator device support 80 will be installed with open cavity 89 facing downwards relative to air flow.

Each of the three ion generators 2 can include one or more optional tabs 87, wings or brackets that extend from a side of the ion generators 2 between first wall 82 and third wall 86. A securing mechanism, such as a screw, nail, rivet, Pem® fastener or other substantially rigid element can secure the tab 87, and ion generator 2, to at least one of the first wall 82 and the third wall 86. In other embodiments, the ion generators 2 can be adhered to one or both of the first wall 82 and the third wall 86 and/or be secured by another mechanical element connected to one or both of the first wall 82 and the third wall 86 that is configured to reduce or stop movement of the ion generators along the length of ion generator device support 80.

Also as seen in FIG. 8A, an optional securing element 83 maintains first wall 82 and third wall 86 in contact with ion generator 3. Securing element 83 can be any suitable element capable of maintaining first wall 82 in relation to third wall 86, such as a screw, rivet, nail, an adhesive, Pem® fastener, or the like. In this embodiment one securing element 83 is shown, but in other embodiments, zero, two or more securing elements 83 can extend from first wall 82 to third wall 86. One or both of the first wall 82 and the third wall 86 can include a corresponding opening or hole to receive each securing element 83.

In this embodiment, the third wall 86 can include a first portion and a second portion, such that when the ion generator device 2 is retained within the open cavity 89, the ion generator device 2 being adjacent the first portion of the third wall 86 and one or more wires 85 connecting the ion generator device 2 to a power supply (not shown), external to the ion generator device support 80 and being adjacent to the second portion of the third wall 86.

As shown in FIG. 8B and subsequent figures, the first wall 82 is substantially parallel to the third wall 86, but, in other embodiments, first wall 82 and third wall 86 can be formed at relative angles to each other.

Also as shown in FIG. 8B and subsequent figures, the second wall 84 has a relatively small radius of curvature, but, in other embodiments the radius of curvature of second wall 84 can be smaller or larger. Also, second wall 84 can be any other suitable shape other than circular, such as elliptical.

First wall 82, second wall 84 and third wall 86 can be formed of the same material, or of different materials from each other. The same or different materials can be any suitable material, including suitable plastics, such as polycarbonates, vinyls, polyethylenes, polyvinyl chloride, polypropylene, acrylonitrile butadiene styrene (ABS) and polystyrene, suitable metals including galvanized steel, stainless steel and aluminum, natural and synthetic rubbers, and combinations thereof.

One or more of first wall 82, second wall 84 and third wall 86 can be formed of a resilient material, such that when they are compressed, deformed, distorted, bent or stretched, they have the capacity to spring back, rebound or return substantially to its original, or nearly original, shape or position.

In this embodiment three ion generator devices 2 are shown, but in other embodiments, ion generator device support 80 can include, one ion generator, two ion generator, or up to several tens of ion generator devices.

In FIG. 8B, a side view of ion generator device support 80 is shown.

Figure 8C:
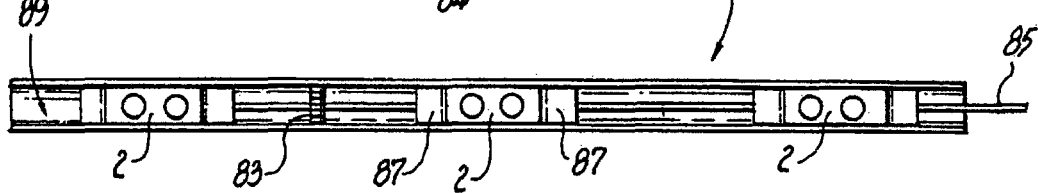

In FIG. 8C, a side or bottom view of a portion of ion generator device support 80 is shown, specifically, the open cavity 89, such that the second wall 84 is visible (where the ion generator devices are not mounted). In FIG. 8C the edge vertically higher is third wall 86.

Figure 8D:
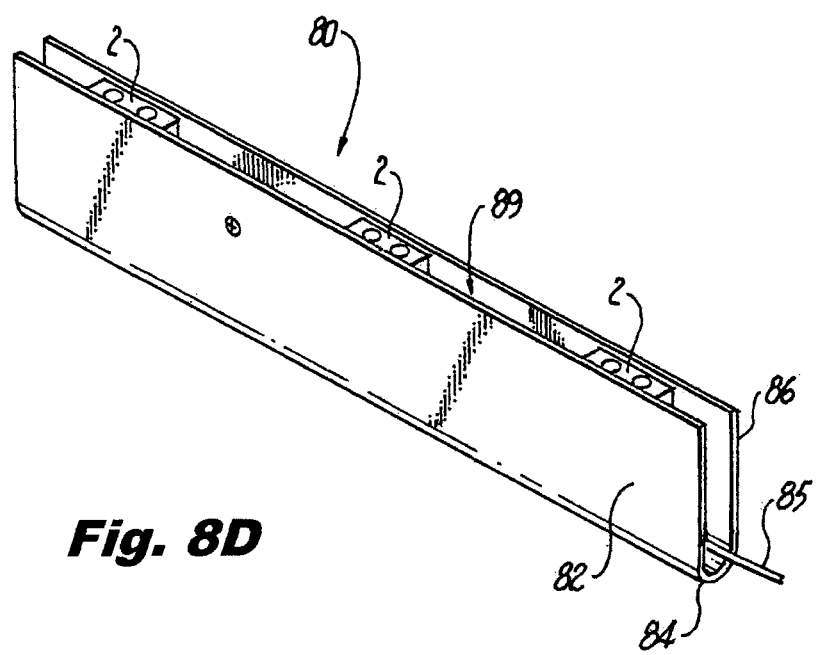

In FIG. 8D, a perspective view of ion generator device support 80 is shown.

Throughout the application, each ion generator device support can be any suitable length capable of retaining one or more ion generator devices on, in, or a combination of on and in HVAC elements, including but not limited to RTUs, AHUs, FCUs, VRVUs, VRFUs, and PTAC units, and also including heat pumps, ducts, air inlets, and air outlets.

Throughout the application, each ion generator device support can be of a length between about six inches and about fifteen feet, with this range including all distances within the range. In other aspect of the disclosure, the length can be between about eighteen inches and about ten feet.

In each embodiment of the application, each ion generator device support can include a single ion generator device up to several tens of ion generator devices.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

What is claimed:

1. An ion generator device support configured to retain an ion generator device, the ion generator device having a first portion containing electrodes and a second portion, the support comprising:

a first wall;
a second wall extending from the first wall; and
a third wall extending from the second wall opposed to the first wall, wherein when the ion generator device is retained in the support, the electrodes are exposed from the support and an edge of the first wall and an edge of the third wall that form an opening;
wherein at least a portion of the first wall extends from the second wall by a smaller distance than a corresponding portion of the third wall extends from the second wall.

2. The support of claim 1, wherein the second wall extends orthogonally from the first wall and a third wall extends orthogonally from the second wall.

3. The support of claim 1, wherein the third wall extends a distance D from the second wall, and wherein the distance D is greater than a length of the ion generator device.

4. The support of claim 3, wherein the third wall has a first portion and a second portion, wherein when retained, the ion generator device is adjacent the first portion and wires connecting the ion generator device to a power supply being adjacent to the second portion.

5. The support of claim 1, wherein the first portion of the ion generator device extends beyond the at least the portion of the first wall.

6. An ion generator device support configured to retain an ion generator device, the ion generator device having a first portion containing electrodes and a second portion, the support comprising:
a first wall;
a cover wall, the cover wall extending orthogonally from the first wall, the cover wall extending along from a first portion of the first wall and not extending along from a second portion of the first wall;
a second wall extending from the first wall;
a third wall extending from the second wall opposed to the first wall, wherein the first wall extends a smaller distance from the second wall than the third wall; and
a fourth wall extending orthogonally from the third wall, wherein a substantially open cavity is defined by the fourth wall, the third wall and an edge of the second portion of the first wall, and a substantially closed cavity is defined by the first wall, the cover wall, the second wall and the third wall, and wherein the first portion of the ion generator device is retained within the substantially open cavity.

7. The support of claim 6, wherein the second wall extends orthogonally from the first wall and a third wall extends orthogonally from the second wall.

8. The support of claim 6, wherein the cover wall extends a majority of the distance between the first wall and the third wall.

9. The ion generator device support of claim 1, further comprising a fourth wall extending orthogonally from the third wall, wherein a cavity is further defined by the fourth wall, the third wall and an edge of the second portion of the first wall, and a substantially closed cavity is defined by the first wall, the second wall and the third wall, and wherein the first portion of the ion generator device is retained within the substantially closed cavity.

10. The ion generator device support of claim 1, further comprising a cover wall, the cover wall extending orthogonally from the first wall, the cover wall extending along from a first portion of the first wall and not extending along from a second portion of the first wall.

11. The ion generator device support of claim 10, wherein the cover wall extends a majority of the distance between the first wall and the third wall.

12. The ion generator device support of claim 10, further comprising a fourth wall extending orthogonally from the third wall, wherein a substantially open cavity is defined by the fourth wall, the third wall and an edge of the second portion of the first wall, and a substantially closed cavity is defined by the first wall, the cover wall, the second wall and the third wall, and wherein the first portion of the ion generator device is retained within the substantially open cavity.

13. The ion generator device support of claim 1, wherein the second wall is curved.

14. The ion generator device support of claim 1, wherein the support is configured to retain a plurality of ion generator devices.

15. The support of claim 14 wherein when the plurality of ion generator devices are retained, the plurality of ion generator devices are aligned.

16. The ion generator device support of claim 1, wherein when retained, a face of the first portion of the ion generator device is aligned with the respective edge of the third wall, and the edge of the first wall abuts a portion of the ion generator device.

17. The ion generator device support of claim 1, wherein the first wall is secured to the third wall with at least one securing element.

18. The ion generator device support of claim 6, wherein the second wall is curved.

19. The ion generator device support of claim 6, wherein the support is configured to retain a plurality of ion generator devices.

20. The support of claim 19, wherein when the plurality of ion generator devices are retained, the plurality of ion generator devices are aligned.

21. The ion generator device support of claim 6, wherein when retained, a face of the first portion of the ion generator device is aligned with the respective edge of the third wall, and an edge of the first wall abuts a portion of the ion generator device.

22. The ion generator device support of claim 6, wherein the first wall is secured to the third wall with at least one securing element.

* * * * *